United States Patent
Bruder et al.

(10) Patent No.: US 7,277,524 B2
(45) Date of Patent: Oct. 2, 2007

(54) METHOD FOR DETECTING AND VISUALIZING DYNAMIC PROCESSES IN AN OBJECT VOLUME

(75) Inventors: Herbert Bruder, Hoechstadt (DE); Thomas Flohr, Uehlfeld (DE); Ernst Klotz, Uttenreuth (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 148 days.

(21) Appl. No.: 11/169,913

(22) Filed: Jun. 30, 2005

(65) Prior Publication Data

US 2006/0018424 A1    Jan. 26, 2006

(30) Foreign Application Priority Data

Jul. 1, 2004    (DE) ............ 10 2004 031 984

(51) Int. Cl.
*A61B 6/00*    (2006.01)

(52) U.S. Cl. .......................... 378/15; 378/4

(58) Field of Classification Search ............ 378/4–20, 378/210, 901
See application file for complete search history.

(56) References Cited

U.S. PATENT DOCUMENTS

| | | | | |
|---|---|---|---|---|
| 5,974,108 A | * | 10/1999 | Taguchi et al. | 378/4 |
| 6,466,640 B1 | * | 10/2002 | Taguchi | 378/15 |
| 2002/0118790 A1 | * | 8/2002 | Pan et al. | 378/8 |
| 2004/0174960 A1 | * | 9/2004 | Hsieh et al. | 378/210 |

FOREIGN PATENT DOCUMENTS

WO    WO98/36690    8/1998

* cited by examiner

*Primary Examiner*—Courtney Thomas
*Assistant Examiner*—Alexander Taningco
(74) *Attorney, Agent, or Firm*—Harness, Dickey & Pierce, PLC

(57) ABSTRACT

A method is disclosed for a multislice computer assisted tomograph, capable of carrying out a spiral scan of an object volume with a pitch p selected to be small enough that each slice of the object volume is multiply detected during the spiral scan. The method includes calculating, using measured data of two temporally consecutive at least one of revolutions and half revolutions, an image of the object volume from which a change inside the object volume between the two temporally consecutive at least one of revolutions and half revolutions is directly visible. An embodiment of the method can permit, for example, the detection and visualization of dynamic processes with an enhanced time resolution.

20 Claims, 2 Drawing Sheets

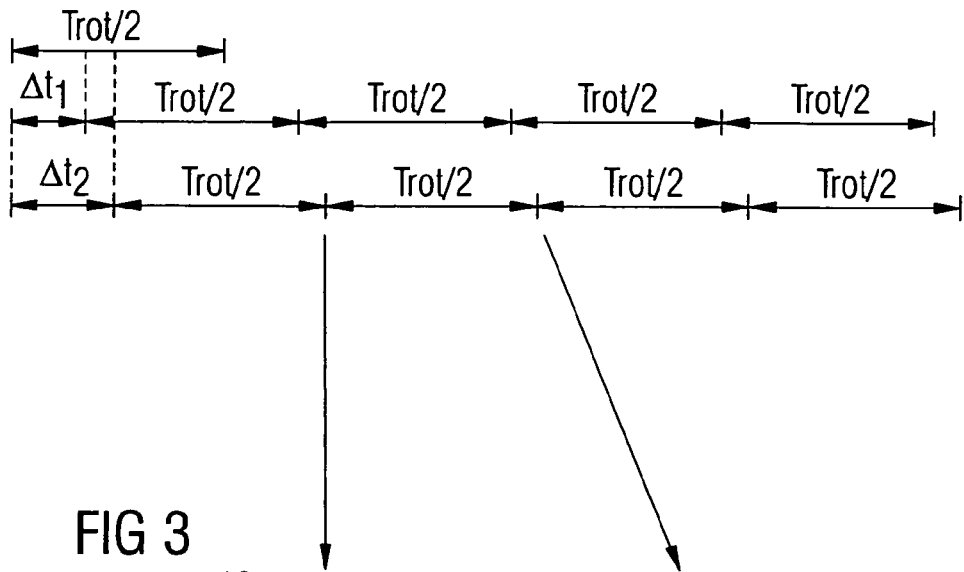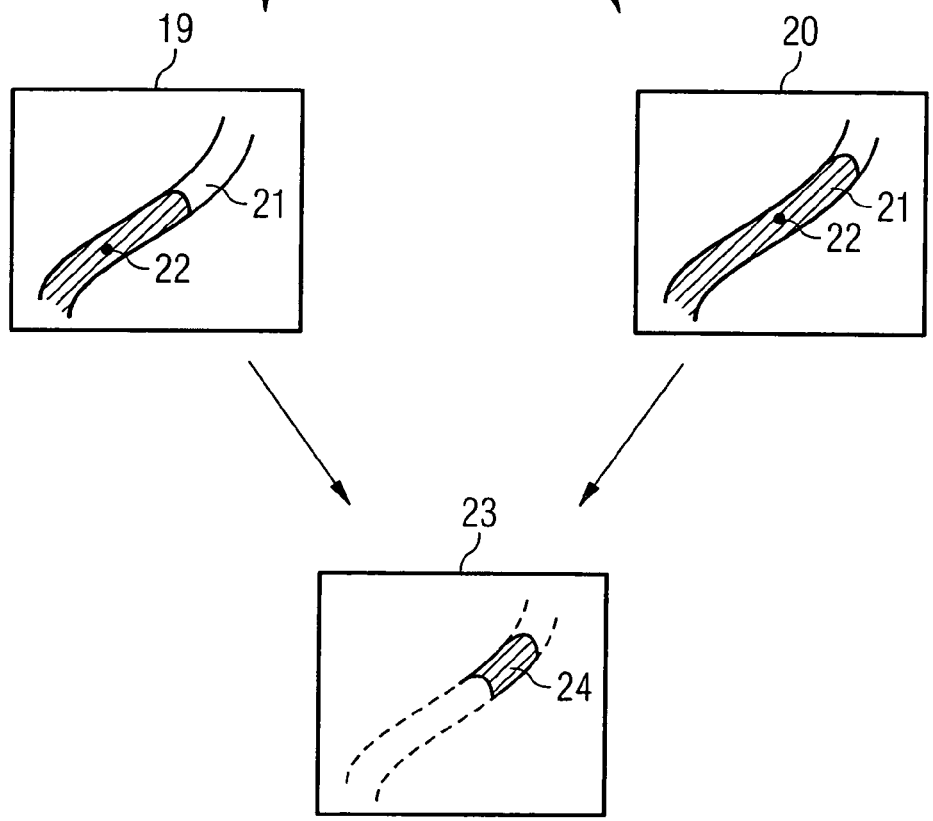

METHOD FOR DETECTING AND VISUALIZING DYNAMIC PROCESSES IN AN OBJECT VOLUME

The present application hereby claims priority under 35 U.S.C. §119 on German patent application number DE 10 2004 031 984.7 filed Jul. 1, 2004, the entire contents of which is hereby incorporated herein by reference.

FIELD

The present invention generally relates to a method for detecting and visualizing dynamic processes in an object volume, in particular inside the human body, by using a computer assisted tomography for example.

BACKGROUND

Volume images of the interior of an examination object can be detected and displayed with the aid of modern imaging medical apparatus, such as computer assisted tomographs. X-ray projections at various angles are recorded by rotating an X-ray source about a system axis, the so-called z-axis, running through the object volume. Slice or volume images of the object volume can then be reconstructed, for example by using the methods of filtered back projection, from the measured data of the recorded projections.

During an examination with the aid of a computer assisted tomograph, the patient's support table is moved along the system axis in order to detect a relatively large volumetric region. In the case of a sequential scan, the movement of the patient table is performed in steps, no measured data being acquired during the movement. In the case of a spiral scan, the patient table is moved continuously with measured data being acquired at the same time.

Each scan in this case includes a number of complete revolutions of the computer assisted tomograph, that is to say a number of complete rotations of the rotary frame of the computer assisted tomograph about the system axis.

In order to detect an object volume completely, it is necessary to adapt the feed of the support table to the slice thickness detected in each case per revolution with the aid of the computer assisted tomograph. This is expressed by way of the so-called pitch, which specifies the ratio between the feed of the patient table per complete revolution of the rotary frame and the slice thickness of the total slice detected by a revolution. In the case of multislice computer assisted tomographs, this thickness of the detected total slice corresponds to the extent of the detector array in a z-direction. Conventional measurements with the aid of computer assisted tomographs are carried out in this case with a pitch>1 in order to achieve a scanning time that is as short as possible.

A quick scanning time plays an important role in the detection of dynamic processes in the object volume. On the one hand, images without movement artifacts are to be obtained thereby. On the other hand, it is also desirable to be able to be carry out time-resolved measurements by detecting a number of slice and/or volume images in a short time interval. Thus, it is known for the purpose of time-resolved measurement of the functional contrast agent profile during the examination of a patient to apply a multiscan technique in which sequential scans are carried out in multiple sequence at a fixed imaging position.

SUMMARY

An object of an embodiment of the present invention resides in specifying a method for detecting and visualizing dynamic processes in an object volume with the aid of which it is possible to implement an enhanced time resolution.

In the present method of an example embodiment, a spiral scan of the object volume is carried out with the aid of a multislice computer assisted tomograph with a pitch p which is selected to be so small that each slice of the object volume is detected multiply during the spiral scan. After, or still during the acquisition of measured data, measured data of a number of temporally consecutive revolutions or half revolutions are used to calculate and display one or more images of the object volume from which a change inside the object volume between temporally consecutive revolutions or half revolutions is visible.

In an example refinement of the method, a number of temporally consecutive half revolution data records are calculated slicewise. The temporal resolution is determined in this case by the time duration Trot/2 for a half revolution of the computer assisted tomograph, namely for a half rotation of the rotary frame about the system axis.

The reconstruction can be performed advantageously for different time phases that are prescribed by different time delays $\Delta t$, in which case $0 \leq \Delta t < T_{rot}/2$.

By selecting the pitch p of the spiral scan in the specified way, each image element or voxel of the object volume is redundantly scanned in a number of neighboring half revolutions of the rotary frame of the computer assisted tomograph, also denoted as half revolutions of the computer assisted tomograph in the present patent application. It is possible as a result to reconstruct separate image data, which correspond to different times during the spiral scan, from the same slice or the same voxel. By calculating separate slice images or volume images of the same object volume from consecutive revolutions or half revolutions, it is possible to detect and visualize dynamic processes inside the object volume with a high time resolution.

The spiral pitch p, that is to say the table feed per revolution referred to the detector length of the computer assisted tomograph in the z-axis, is selected, for example, as p=2/n, n being an integral value>2. The value n corresponds to the number of instants at which the image element considered is to be recorded.

The slice images or volume images of the object volume may be, for example, calculated and displayed from the measured data or image data of in each case, two temporally consecutive revolutions or half revolutions such that a change between the temporally consecutive revolutions or half revolutions inside the object volume is directly visible from the images. This can be performed, for example, by displaying the changed image regions in color or on their own.

The calculation of the images of the object volume can be carried out in different ways, a reconstruction of image data from the measured data or preprocessed measured data being a constituent of each calculation. In one refinement of an embodiment of the present method, direct and complementary projections of in each case two half revolutions that are neighboring, that is to say directly consecutive, are subtracted in order firstly to obtain difference data. The image is subsequently reconstructed from the difference data. In this case, each slice image or volume image displayed consequently shows only the temporal change with reference to the instant of the directly preceding half revolution.

In a further refinement of an embodiment of the present method, the image data are firstly reconstructed in each case from the measured data of the half revolutions. Temporal density gradients in the image signal can then be displayed from the image data of in each case temporally neighboring half revolutions by forming the difference values in a pixelwise fashion. Of course, it is also possible to evaluate the density of the image data of the reconstructed half revolutions with reference to pixels, and to carry out the comparison with correspondingly preceding image data.

BRIEF DESCRIPTION OF THE DRAWINGS

The present method is explained briefly again below with the aid of an example embodiment in conjunction with the drawings, in which:

FIG. 2 shows a schematic of temporal and spatial parameters during the carrying out of an embodiment of the present method; and FIG. 3 shows a highly schematic for illustrating the calculation of images of the object volume in accordance with one embodiment of the method.

DETAILED DESCRIPTION OF THE EXAMPLE EMBODIMENTS

Figure 1:
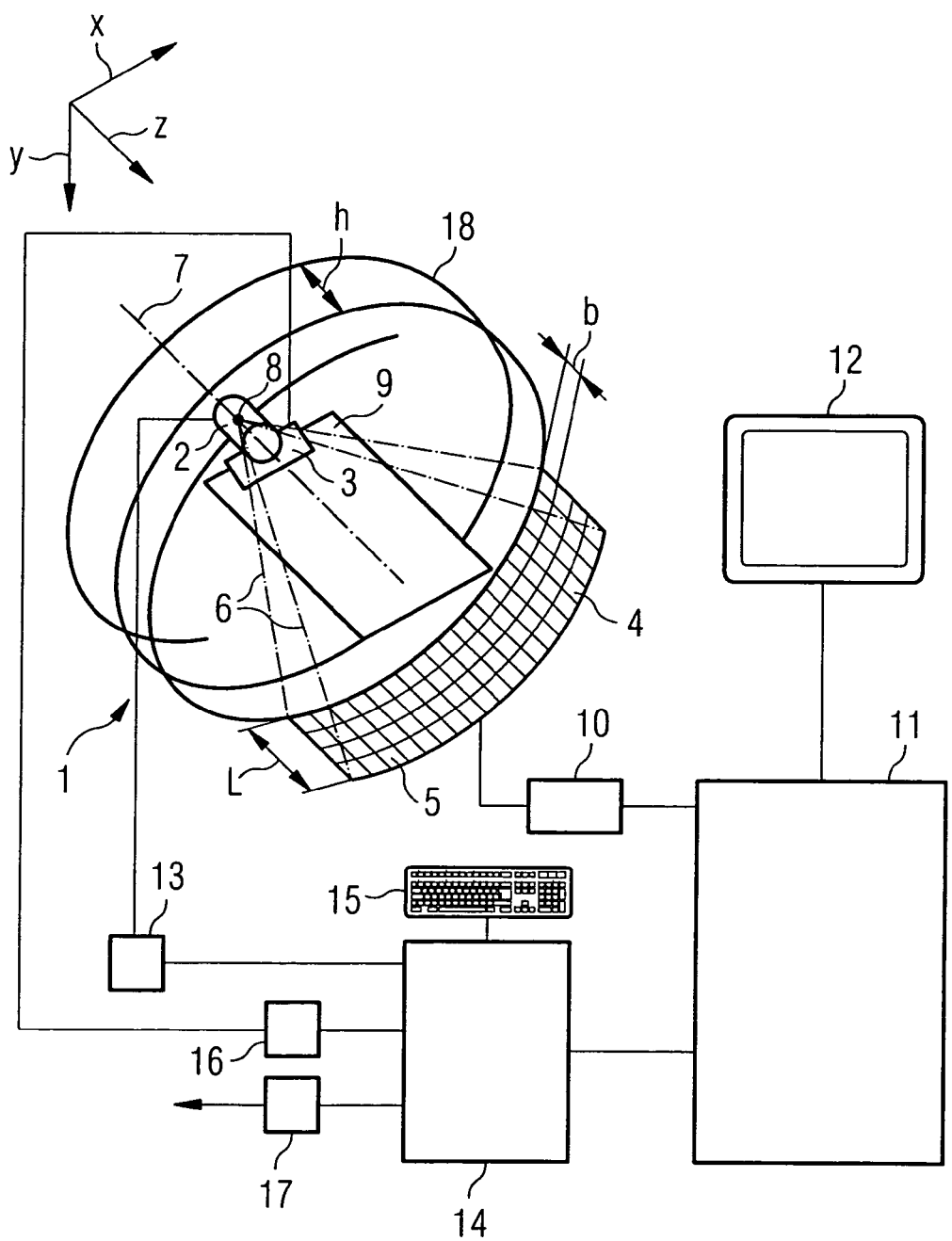
FIG. 1 shows a schematic of a multislice computer assisted tomograph for carrying out an embodiment of the present method.

A multislice computer assisted tomograph 1 as can be used for carrying out an embodiment of the present method is illustrated schematically in FIG. 1. The measuring arrangement of this computer assisted tomograph 1 has an X-ray emitter 2 with an insertion device 3 in front thereof and near the source, and an X-ray detector 5 designed as a multirow or planar array of a number of rows and columns of detector elements 4.

For the sake of clarity, only four rows of detector elements 4 are illustrated in the illustration of FIG. 1. However, the X-ray detector may, and even preferably may have further rows of detector elements 4. The X-ray detector 5 can be designed as a solid-state matrix detector system, in particular as a flat-image detector and/or as a detector that comprises a scintillator layer and an assigned electronic photoreceiver matrix.

The X-ray emitter 2 with the insertion device 3, on the one hand, and the X-ray detector 5 with its radiation diaphragm (not illustrated), on the other hand, are fitted on a rotary frame situated opposite one another in such a way that a pyramidal X-ray beam that emanates from the X-ray emitter 2 during operation of the computer assisted tomograph 1 and is inserted by the settable insertion device 3, and whose edge rays are denoted in FIG. 1 by the reference numeral 6, strikes the X-ray detector 5. The rotary frame can be set rotating about a system axis 7 by way of a drive device (not illustrated).

The system axis 7 runs parallel to the z-axis of a three-dimensional rectangular coordinate system illustrated in FIG. 1. The columns of the X-ray detector 5 likewise run in the direction of the z-axis, while the rows, whose width b is measured in the direction of the z-axis and is, for example, 1 mm, run transverse to the system axis 7 or the z-axis.

In order to be able to bring the examination object, for example the patient, into the beam path of the X-ray beam, a support table 9 is provided that can be displaced parallel to the system axis 7, that is to say in the direction of the z-axis.

The displacement is performed in such a way that there is synchronization between the rotary movement of the rotary frame and the translatory movement of the support table 9, it being possible to set the ratio of speed of translation to rotation speed by prescribing a desired value for the feed h of the support table 9 per revolution of the rotary frame. The ratio between the feed h of the support table per revolution of the rotary frame (rotation period Trot) and the total length L of the X-ray detector 5 in the direction perpendicular to the z-axis, that is to say the sum of the widths b of the individual detector rows, is denoted as pitch p.

An object volume of an examination object situated on the support table 9 can be examined by way of volumetric scanning by operating this computer assisted tomograph. In the case of spiral scanning such as is carried out in an embodiment of the present method, many projections are recorded from various projection directions accompanied by rotation of the rotary frame and simultaneous translation of the support table 9 per revolution of the rotary frame. In the process, the focus 8 of the X-ray emitter 2 moves relative to the support table 9 on a spiral track 18.

The measured data, which are read out in parallel during spiral scanning from the detector elements 4 of each active row of the detector system 5 and correspond to the individual projections, are subjected to analog-to-digital conversion in a data conditioning unit 10, serialized and transmitted as raw data to an image computer 11 that displays the result of an image reconstruction or of an image calculation based thereon on the display unit 12, for example a video monitor.

The X-ray emitter 2, for example an X-ray tube, is supplied with the necessary voltages and currents by a generator unit 13. In order to be able to set these to the values respectively required, the generator unit 13 is assigned a control unit 14 with a keyboard 15 that allows the appropriate settings. The remaining operation and control of the computer assisted tomograph 1 is also performed by way of the control unit 14 and the keyboard 15.

It is possible, inter alia, to set the number of the active rows of detector elements 4, and thus the position of the insertion device 3 and of the optional radiation diaphragm, close to the detector, for which purpose the control unit 14 is connected to adjusting units 16, 17 assigned to the insertion device 3 and the optional radiation diaphragm close to the detector. Furthermore, it is possible to set the rotation period $T_{rot}$ required by the rotary frame for a complete revolution.

The displacement path of the support table 9 during a revolution of the rotary frame is defined by the setting of the rotation period $T_{rot}$ together with the feed rate of the support table 9. Taking account of the total length L of the X-ray detector 5 in the z-direction, it follows that the spiral pitch p is also stipulated. In the case of an embodiment of the present method, this pitch p is selected to be so small that each voxel of the object volume of interest is multiply detected during a spiral scan, which includes a number of revolutions of the rotary frame about the system axis.

Given an exemplary definition of the table feed h per revolution of the rotary frame at half the length L/2 of the X-ray detector 5, each voxel or each slice is detected four times in a temporally consecutive fashion. This corresponds to a pitch of p=½. The same voxels of a slice are thereby recorded in each case with the aid of different detector channels in four consecutive half revolutions of the rotary frame. It is possible thereby to use the acquired measured data to carry out four separate image reconstructions with the aid of which the voxels can be displayed at different times.

These image reconstructions for obtaining the image data are performed after or still during the acquisition of measured data, the density values of the corresponding pixels of the reconstructed image data of in each case temporally consecutive half revolutions being subtracted from one another in the present example. The one or more volume images resulting therefrom are displayed to the user on the monitor.

FIG. 2 shows for the purposes of illustration different temporal phases $\Delta t_{1/2}$ in comparison with half the rotation period $T_{rot}/2$ of the rotary frame during this spiral scan. Here, images with the time resolution of $T_{rot}/2$ are obtained in relation to the different phases. During a complete revolution of the rotary frame, the support table moves further only by a fraction of the total length L of the X-ray detector in the z-direction.

An image 19 which is reconstructed from the measured data of a half revolution and the image 20 reconstructed from the measured data of the half resolution following thereupon are shown in FIG. 3 by way of example and in a highly schematic fashion. A vessel 31 in which contrast agent 22 flows in the direction of the arrow is to be seen in the figure solely for the purpose of illustration. The same object slice is detected in two consecutive half revolutions owing to the small pitch p selected in the case of an embodiment of the present method, and so it is possible by forming the differences between the image data of the two images to calculate and display a differential image 23 that shows only the change 24 between the instants of the two half revolutions.

When carrying out spiral scanning of a patient's head, for example, an embodiment of the method can be used to display arteriovenous malformations (AVM) of the cranial vessels both with high spatial resolution and with an adequate temporal resolution. The assessment thereby rendered possible of the degree of the arteriovenous shunt supplies important information for planning therapy. A low-pitch examination that is synchronized with the injection of contrast agent and is carried out in accordance with the present method permits a temporal resolution of the contrast agent influx from which this information can be obtained.

The above described embodiments of the method may further be embodied in a physical device for a multislice computer assisted tomograph, as would be understood by one of ordinary skill in the art, including via use of the disclosed and/or illustrated examples.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for detecting and visualizing dynamic processes in an object volume, the method comprising:
   using a multislice computer assisted tomograph to carry out a spiral scan of the object volume with a pitch p selected to be small enough that each slice of the object volume is multiply detected during the spiral scan; and
   calculating and displaying, using measured data of two temporally consecutive at least one of revolutions and half revolutions, an image of the object volume from which a change inside the object volume between the two temporally consecutive at least one of revolutions and half revolutions is directly visible.

2. The method as claimed in claim 1, wherein a number of images for different temporal phases that are prescribed by time delays $\Delta t < T_{rot}/2$, wherein $T_{rot}/2$ is a time duration of a half revolution, are calculated and displayed in the event of each slice being detected more than twice.

3. The method as claimed in claim 2, wherein difference data are first calculated by forming differences from the measured data of the two temporally consecutive at least one of revolutions and half revolutions, and wherein the image of the object volume is subsequently reconstructed from the difference data.

4. The method as claimed in claim 2, wherein image data are reconstructed from the measured data of the two temporally consecutive at least one of revolutions and half revolutions and wherein the image of the object volume is calculated by forming the differences between the reconstructed image data of the two temporally consecutive at least one of revolutions and half revolutions.

5. The method of claim 4, further comprising:
   displaying the calculated image of the object volume.

6. The method as claimed in claim 2, wherein image data are reconstructed from the two temporally consecutive at least one of revolutions and half revolutions and wherein the image of the object volume is calculated from the reconstructed image data by use of density evaluation and comparison of the image data of the two temporally consecutive at least one of revolutions and half revolutions.

7. The method as claimed in claim 1, wherein the pitch is selected as $p=2/n$, n being an integral value $>2$.

8. The method as claimed in claim 7, wherein difference data are first calculated by forming differences from the measured data of the two temporally consecutive at least one of revolutions and half revolutions, and wherein the image of the object volume is subsequently reconstructed from the difference data.

9. The method as claimed in claim 7, wherein image data are reconstructed from the measured data of the two temporally consecutive at least one of revolutions and half revolutions and wherein the image of the object volume is calculated by forming the differences between the reconstructed image data of the two temporally consecutive at least one of revolutions and half revolutions.

10. The method as claimed in claim 7, wherein image data are reconstructed from the two temporally consecutive at least one of revolutions and half revolutions and wherein the image of the object volume is calculated from the reconstructed image data by use of density evaluation and comparison of the image data of the two temporally consecutive at least one of revolutions and half revolutions.

11. The method as claimed in claim 1, wherein difference data are first calculated by forming differences from the measured data of the two temporally consecutive at least one of revolutions and half revolutions, and wherein the image of the object volume is subsequently reconstructed from the difference data.

12. The method as claimed in claim 1, wherein image data are reconstructed from the measured data of the two temporally consecutive at least one of revolutions and half revolutions and wherein the image of the object volume is calculated by forming the differences between the reconstructed image data of the two temporally consecutive at least one of revolutions and half revolutions.

13. The method as claimed in claim 1, wherein image data are reconstructed from the two temporally consecutive at least one of revolutions and half revolutions and wherein the image of the object volume is calculated from the reconstructed image data by use of density evaluation and comparison of the image data of the two temporally consecutive at least one of revolutions and half revolutions.

14. The method as claimed in claim 1, wherein the image of the object volume is calculated and displayed as volume images.

15. A method for a multislice computer assisted tomograph, capable of carrying out a spiral scan of an object volume with a pitch p selected to be small enough that each slice of the object volume is multiply detected during the spiral scan, the method comprising:

calculating and displaying, using measured data of two temporally consecutive at least one of revolutions and half revolutions, an image of the object volume from which a change inside the object volume between the two temporally consecutive at least one of revolutions and half revolutions is directly visible.

16. The method as claimed in claim 15, wherein a number of images for different temporal phases that are prescribed by time delays $\Delta t < T_{rot}/2$, wherein $T_{rot}/2$ is a time duration of a half revolution, are calculated and displayed in the event of each slice being detected more than twice.

17. The method as claimed in claim 15, wherein the pitch is selected as $p=2/n$, n being an integral value $>2$.

18. A device for a multislice computer assisted tomograph, capable of carrying out a spiral scan of an object volume with a pitch p selected to be small enough that each slice of the object volume is multiply detected during the spiral scan, the device comprising:

means for calculating, using measured data of two temporally consecutive at least one of revolutions and half revolutions, an image of the object volume from which a change inside the object volume between the two temporally consecutive at least one of revolutions and half revolutions is directly visible; and means for displaying the calculated image of the object volume.

19. The device as claimed in claim 18, wherein a number of images for different temporal phases that are prescribed by time delays $\Delta t < T_{rot}/2$, wherein $T_{rot}/2$ is a time duration of a half revolution, are calculated and displayed in the event of each slice being detected more than twice.

20. The device as claimed in claim 18, wherein the pitch is selected as $p=2/n$, n being an integral value $>2$.

* * * * *

UNITED STATES PATENT AND TRADEMARK OFFICE
CERTIFICATE OF CORRECTION

PATENT NO. : 7,277,524 B2
APPLICATION NO. : 11/169913
DATED : October 2, 2007
INVENTOR(S) : Herbert Bruder et al.

It is certified that error appears in the above-identified patent and that said Letters Patent is hereby corrected as shown below:

On the title page, item [73] should read:
-- Assignee: Siemens ~~Aktienbesellschaft~~ Aktiengesellschaft --.

Signed and Sealed this

Eighteenth Day of December, 2007

JON W. DUDAS
*Director of the United States Patent and Trademark Office*